United States Patent
Gifford et al.

(10) Patent No.: US 10,386,276 B2
(45) Date of Patent: Aug. 20, 2019

(54) PHOSPHOPROTEIN DETECTION USING A CHIP-BASED PILLAR ARRAY

(71) Applicant: International Business Machines Corporation, Armonk, NY (US)

(72) Inventors: Stacey M. Gifford, Ridgefield, CT (US); Gustavo A. Stolovitzky, Riverdale, NY (US); Benjamin H. Wunsch, Mt. Kisco, NY (US)

(73) Assignee: International Business Machines Corporation, Armonk, NY (US)

(*) Notice: Subject to any disclaimer, the term of this patent is extended or adjusted under 35 U.S.C. 154(b) by 197 days.

(21) Appl. No.: 15/270,478

(22) Filed: Sep. 20, 2016

(65) Prior Publication Data
US 2018/0080857 A1   Mar. 22, 2018

(51) Int. Cl.
| | |
|---|---|
| *B01D 15/00* | (2006.01) |
| *G01N 1/34* | (2006.01) |
| *B01L 3/00* | (2006.01) |
| *G01N 1/40* | (2006.01) |
| *B01D 15/34* | (2006.01) |
| *G01N 30/00* | (2006.01) |
| *G01N 33/537* | (2006.01) |

(52) U.S. Cl.
CPC .............. *G01N 1/34* (2013.01); *B01D 15/34* (2013.01); *B01L 3/50273* (2013.01); *B01L 3/502753* (2013.01); *B01L 3/502761* (2013.01); *G01N 1/40* (2013.01); *G01N 30/0005* (2013.01); *G01N 33/537* (2013.01); *B01L 2200/0647* (2013.01); *B01L 2200/0652* (2013.01); *B01L 2400/0415* (2013.01)

(58) Field of Classification Search
None
See application file for complete search history.

(56) References Cited

U.S. PATENT DOCUMENTS

| | | |
|---|---|---|
| 6,046,056 A | 4/2000 | Parce et al. |
| 7,476,656 B2 | 1/2009 | Stevens, Jr. et al. |
| | (Continued) | |

OTHER PUBLICATIONS

Huang et al., "Continuous Particle Separation Through Deterministic Lateral Displacement," Science, vol. 304 (May 2004).

(Continued)

*Primary Examiner* — Erik B Crawford
(74) *Attorney, Agent, or Firm* — Vazken Alexanian; Michael J. Chang, LLC (57) ABSTRACT

Techniques for phosphoprotein detection, quantification, and purification using a chip-based pillar array are provided. In one aspect, a method for purifying a protein sample includes: introducing a mixture including the protein sample and an antibody to a nanoDLD array having a plurality of pillars separated by a gap g, wherein the antibody and proteins in the protein sample form antibody-protein complexes having a size that is greater than a size threshold of the nanoDLD array created by the gap g which permits size-based separation of the antibody-protein complexes as the mixture flows through the nanoDLD array; and collecting a purified protein sample containing the antibody-protein complexes from the nanoDLD array. A lab-on-a-chip (LOC) device including the nanoDLD array is also provided.

10 Claims, 12 Drawing Sheets

(56) References Cited

U.S. PATENT DOCUMENTS

| | | | |
|---|---|---|---|
| 7,693,665 B2 | 4/2010 | Zhu et al. | |
| 8,585,971 B2 | 11/2013 | Huang et al. | |
| 9,012,373 B2 | 4/2015 | Boles et al. | |
| 2004/0265938 A1* | 12/2004 | Remacle | C12Q 1/42 435/7.92 |
| 2005/0214130 A1 | 9/2005 | Yang | |
| 2007/0196820 A1* | 8/2007 | Kapur | B01L 3/502746 435/5 |
| 2014/0030788 A1* | 1/2014 | Chen | B01L 3/502707 435/177 |
| 2016/0047735 A1 | 2/2016 | Grisham et al. | |
| 2016/0144405 A1 | 5/2016 | Astier et al. | |

OTHER PUBLICATIONS

Inglis, et al., "Critical particle size for fractionation by deterministic lateral displacement," Lab Chip, 6, 655-658 (Mar. 2006).

Bruin, "Recent developments in electrokinetically driven analysis on microfabricated devices," Electrophoresis, 21, pp. 3931-3951 (Dec. 2000).

M. Cerny et al., "Advances in purification and separation of posttranslationally modified proteins," Journal of Proteomics, vol. 92, Jun. 2013, pp. 2-27.

M. Mann et al., "Analysis of protein phosphorylation using mass spectrometry: deciphering the phosphoproteome," Trends in Biotechnology, vol. 20, No. 6, Jun. 2002, pp. 261-268.

N. Li et al., "On-chip continuous blood cell subtype separation by deterministic lateral displacement," 2nd IEEE International Conference on Nano/Micro Engineered and Molecular Systems, Jan. 2007, pp. 932-936.

Marusyk et al., "Tumor heterogeneity: causes and consequences," Biochim Biophys Acta. 1805, pp. 1-28, Jan. 2010.

\* cited by examiner

PHOSPHOPROTEIN DETECTION USING A CHIP-BASED PILLAR ARRAY

FIELD OF THE INVENTION

The present invention relates to protein detection, quantification, and purification, and more particularly, to phosphoprotein detection, quantification, and purification using a chip-based pillar array.

BACKGROUND OF THE INVENTION

Phosphorylation is an important signaling mechanism that occurs through post-translational modification of proteins. Kinases are enzymes that add a phosphate group to serine, threonine, tyrosine, histidine, arginine, and lysine amino acid residues of their substrate proteins.

Phosphorylation can have several effects including activation, inactivation, structural changes, binding to other proteins, and protein degradation. Kinase upregulation and activation is common in many diseases including cancers. In fact, the first oncogene identified was Src, a tyrosine kinase which drives cancer by increasing phosphorylation and signaling through downstream substrates.

Therefore, phosphorylated proteins or phosphoproteins are important biomarkers and their detection is critical in the study, diagnosis, and treatment of disease. Furthermore, cell-to-cell heterogeneity in cancers has recently been identified as an important factor in drug resistance. Therefore, there is a need for single-cell and single-molecule analysis of phosphoproteins.

Existing methods to detect phosphorylated proteins include antibody-based methods such as immunofluorescence, enzyme-linked immunosorbent assay (ELISA), flow cytometry, Western blotting, radiometric kinase assays, and mass spectrometry. Kinase assays are generally performed in vitro and require the use of purified kinase. Thus, kinase assays are not a useful technique for detecting changes in substrate phosphorylation under different in vivo conditions. Immunofluorescence can detect cell-to-cell heterogeneity, however sensitivity and antibody performance are frequent issues. Further, immunofluorescence and Western blotting are generally qualitative techniques.

ELISA can be quantitative, but the volumes required for analysis do not allow for single-cell studies. Flow cytometry does allow for single-cell studies and quantification of the number of cells labeled, but does not allow for single-molecule detection and quantification within each cell. Additionally, flow cytometry of internal phosphoproteins requires fixation and permeabilization of cells and subsequent recovery of proteins is not possible. Finally, mass spectrometry can be sensitive and qualitative, but due to the negative charge of phosphate groups, phosphorylated proteins are often difficult to ionize and detect over background peaks.

Therefore, a more robust and quantitative method for the detection and collection of phosphoproteins is needed.

SUMMARY OF THE INVENTION

The present invention provides techniques for phosphoprotein detection, quantification, and purification using a chip-based pillar array. In one aspect of the invention, a method for purifying a protein sample is provided. The method includes: introducing a mixture including the protein sample and an antibody to a nanoscale deterministic lateral displacement (nanoDLD) array having a plurality of pillars separated by a gap g, wherein the antibody and proteins in the protein sample form antibody-protein complexes having a size that is greater than a size threshold of the nanoDLD array created by the gap g which permits size-based separation of the antibody-protein complexes as the mixture flows through the nanoDLD array; and collecting a purified protein sample containing the antibody-protein complexes from the nanoDLD array.

In another aspect of the invention, a lab-on-a-chip (LOC) device for purifying a protein sample is provided. The LOC device includes: a nanoDLD array having a plurality of pillars separated by a gap g; and an antibody preloaded onto the LOC device upstream from the nanoDLD array, wherein the antibody and proteins in the protein sample form antibody-protein complexes having a size that is greater than a size threshold of the nanoDLD array created by the gap g which permits size-based separation of the antibody-protein complexes as the mixture flows through the nanoDLD array.

A more complete understanding of the present invention, as well as further features and advantages of the present invention, will be obtained by reference to the following detailed description and drawings.

DETAILED DESCRIPTION OF PREFERRED EMBODIMENTS

Provided herein are techniques that employ a nanoscale deterministic lateral displacement (nanoDLD) array to sort phosphorylated proteins (i.e., phosphoproteins) based on their size and charge. For detection alone, fluorescent antibodies (Ab) specific to the phosphoprotein can be used which bind to phosphorylated proteins effectively increasing their size and making the phosphoprotein-Ab complex "bump" out of the "zig-zag" flow stream. The nanoDLD arrays described herein are part of a diagnostic silicon chip that may also be referred to herein as a lab-on-a-chip or LOC device.

For detection and purification, bead-coupled phosphospecific antibodies can be used to amplify the size of targeted phosphoproteins and bump them to a higher threshold than all contaminating particles, and which permits the phosphoprotein-bead-Ab complex to flow straight through the array. For phosphorylation sites lacking a specific antibody, a general antibody to the target protein can be coupled with charge-based separation to first sort phosphorylated and non-phosphorylated target proteins out of the flow stream, and then to separate the negatively-charged phosphorylated proteins from their non-phosphorylated counterparts.

Fluorescent beads and fluorescently-labeled antibodies allow for previously unavailable single-molecule detection and quantification of phosphorylated proteins. Single molecule detection allows for a higher-sensitivity assay than even ELISA (which requires signal amplification) or mass spectrometry as ionization is not an issue. The volume of the nano-DLD array is amenable to handling the volume of a single eukaryotic cell, making the present approach amenable to single-cell analysis.

Figure 1:
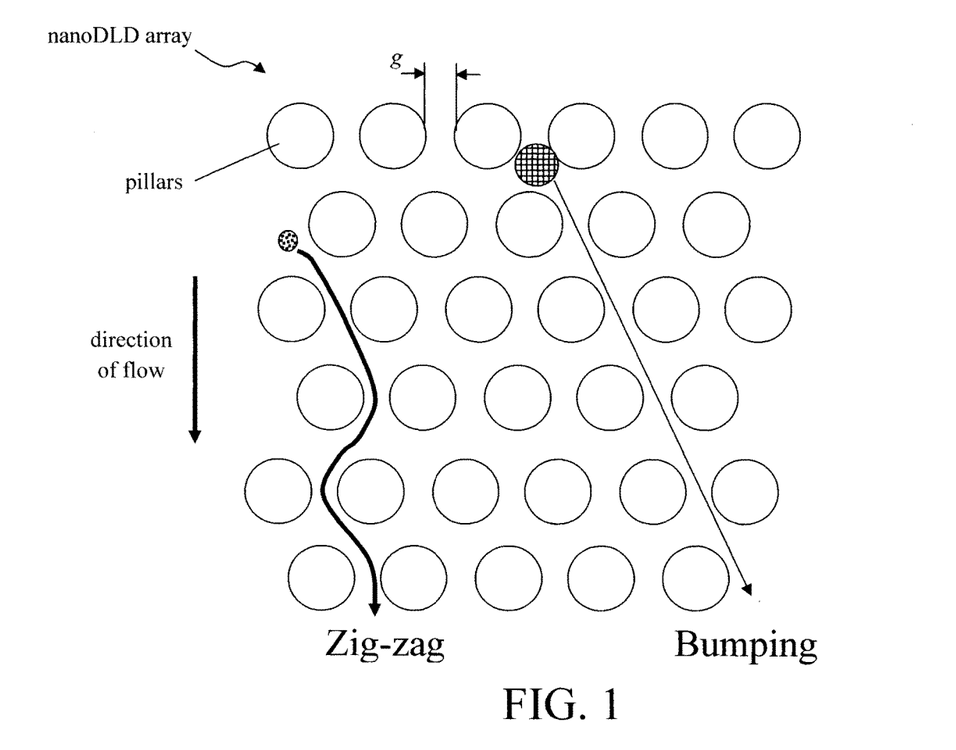
FIG. 1 is a diagram illustrating an exemplary nanoDLD array being used to separate particles based on size according to an embodiment of the present invention.

The present techniques are now described in detail by way of reference to FIGS. 1-9. Referring to FIG. 1, a nanoDLD array is shown which consists of an array of pillars. Standard lithography and etching techniques can be utilized to pattern the pillars. By way of example only, the pillar array features can be defined in a silicon dioxide ($SiO_2$) hard mask on a bulk silicon substrate. Following hard mask definition, all features can then be transferred to the substrate using an etch such as reactive-ion etching (RIE). See, for example, U.S. patent application Ser. No. 14/700,939 by Astier et al., entitled "Immunoassay for Detection of Virus-Antibody Nanocomplexes in Solution by Chip-Based Pillar Array" (hereinafter "U.S. patent application Ser. No. 14/700,939"), the contents of which are incorporated by reference as if fully set forth herein.

As shown in FIG. 1, the pillars are spaced by a specified gap g. This gap size creates a size threshold where particles larger than the threshold are "bumped" to the collection wall and all other particles below that threshold pass through the array in a "zig-zag" mode. See FIG. 1.

The pillar arrays implemented herein are, what is known in the art as, deterministic lateral displacement (DLD) pillar arrays. According to an exemplary embodiment, gap g between the pillars is from about 1 micrometer (µm) to about 5 µm, and ranges therebetween, which sorts particles larger than 500 nm in size and "bumps" them to the right side of the array. The principles behind the mechanism of bumping are described, for example, in Huang et al., "Continuous Particle Separation Through Deterministic Lateral Displacement," Science, vol. 304 (May 2004) (hereinafter "Huang"); and Inglis, et al., "Critical particle size for fractionation by deterministic lateral displacement," Lab Chip, 6, 655-658 (March 2006) (hereinafter "Inglis"), the contents of each of which are incorporated by reference as if fully set forth herein.

FIG. 1 illustrates the passage of two sized particles through the nanoDLD array. One of the particles (the particle on the right) is larger than the size threshold (defined by gap g between the pillars) and the other particle (the particle on the left) is smaller than the size threshold. As shown in FIG. 1, particles larger than the threshold are "bumped", while all other particles below that threshold pass through the array in a "zig-zag" mode. The "bumped" and "zig-zag" fractions can be separately collected from the array.

An arrow is used to indicate the direction of flow through the array. For instance, in this example, a sample is introduced at the top of the array. Particle separation occurs as the sample flows through the array from top to bottom.

Thus, flow through the nanoDLD array of FIG. 1 allows for separation of particles by size. For instance, in an exemplary embodiment described below, fluorescently-labeled phospho-specific antibodies are used to separate phosphoproteins from non-phosphorylated proteins based on size. Specifically, binding of the fluorescently-labeled phospho-specific antibodies to the phosphoproteins increases the particle size above the threshold. Thus, the phospho-specific antibody+phosphoproteins complexes are bumped by the array, and can be separately collected, analyzed, purified, etc. The non-phosphorylated proteins (without bound antibody) remain below the threshold size and pass through the array in the zig-zag mode.

Figure 2:
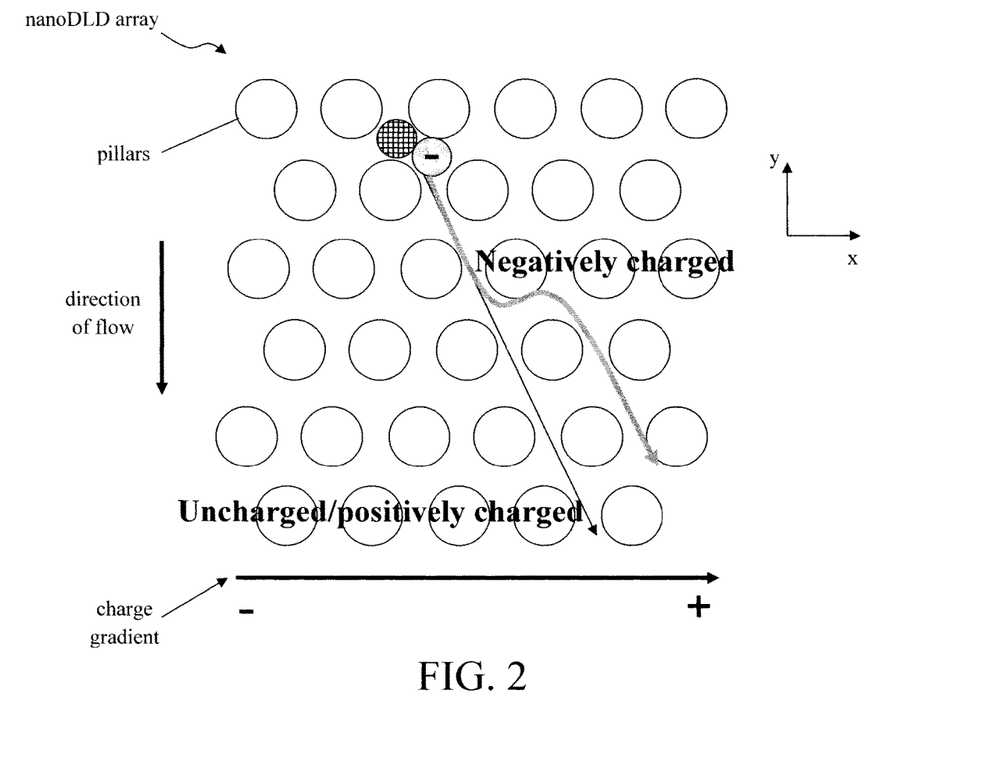
FIG. 2 is a diagram illustrating a charge separation being used to enhance particle separation according to an embodiment of the present invention.

To increase the resolution of separation of particles by size, a charge can be generated perpendicular to the direction of flow for charge separation. See FIG. 2. As shown in FIG. 2, a charge is applied to the array whereby the particles moving along the direction of flow (i.e., along the y-direction) experience a negative to positive charge gradient (along the x-direction). As a result, negatively charged particles will tend to move more to the right side of the array (along the x-direction) toward the positive end of the gradient, while positively or uncharged particles will tend to move toward the left side of the array (along the x-direction) toward the negative end of the gradient. This is what is referred to herein as "charge separation." According to an exemplary embodiment, the charge is applied using embedded electrodes to electrophoretically move particles along the axis perpendicular to flow. The use of electrophoresis on chip is described, for example, in Bruin, "Recent developments in electrokinetically driven analysis on microfabricated devices," Electrophoresis, 21, pgs. 3931-3951 (December 2000), the contents of which are incorporated by reference as if fully set forth herein.

Use of a charge gradient for phosphoproteins separation is advantageous since phosphate groups are negatively charged. Thus, a sample containing both phosphorylated and non-phosphorylated proteins can be separated by size using fluorescently-labeled phospho-specific antibodies as described in accordance with the description of FIG. 1 above while, additionally, a charge gradient is applied to fine tune the separation wherein only the fraction at the (in this example) far right of the array will be collected. As a result, the sample collected in this manner will contain predominantly (negatively charged) phosphoproteins+antibody complexes.

Figure 3:
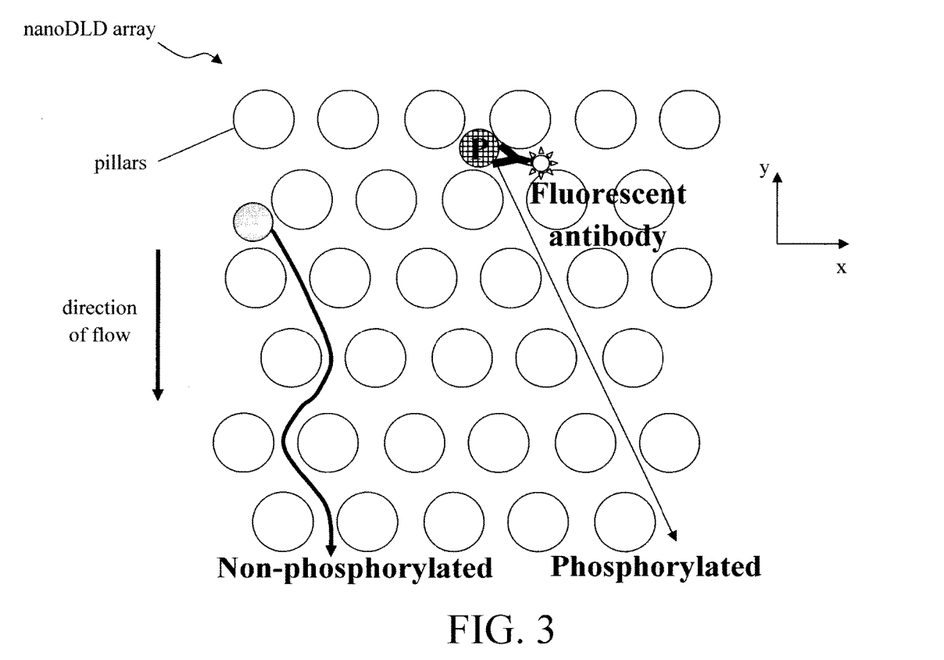
FIG. 3 is a diagram illustrating the present nanoDLD array being used for detection, quantification, and purification of phosphoproteins with a fluorescently-labeled phospho-specific antibody according to an embodiment of the present invention.
Figure 4:
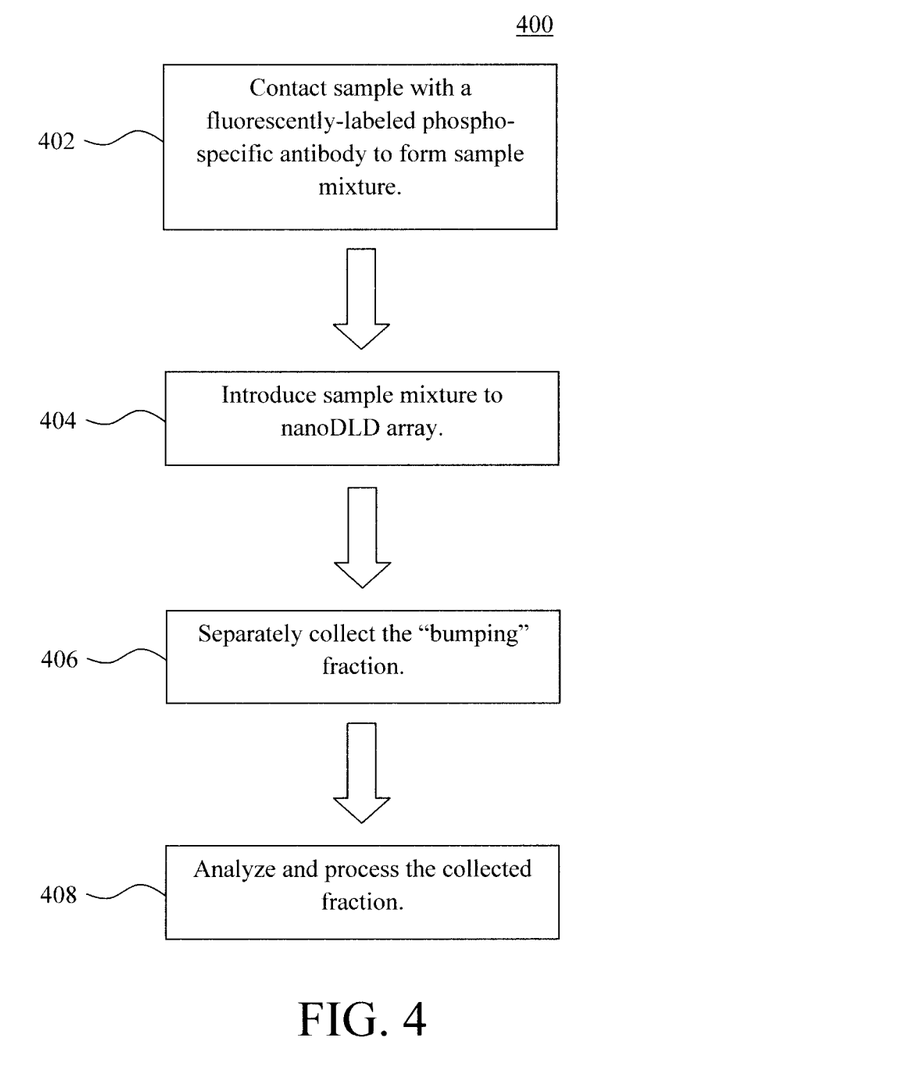
FIG. 4 is a diagram illustrating an exemplary methodology for detection, quantification, and purification of phosphoproteins with a fluorescently-labeled phospho-specific antibody according to an embodiment of the present invention.

The following examples build upon these notions of size and charge-based separation for the detection, quantification, and purification of phosphoproteins. For example, FIG. 3 illustrates detection and quantification of phosphoproteins with a fluorescently-labeled phospho-specific antibody. FIG. 3 schematically illustrates the steps carried out in methodology 400 of FIG. 4. Thus, FIG. 3 and FIG. 4 are described together.

In step 402 of methodology 400, a sample is contacted with a fluorescently-labeled phospho-specific antibody. According to an exemplary embodiment, step 402 is carried out simply by mixing the (fluid) sample with a solution containing the fluorescently-labeled phospho-specific antibody to form a sample mixture.

By way of example only, the samples analyzed using the present techniques can include biological samples such as cell lysate, in vitro samples, blood, and other bodily fluids. A variety of fluorescent tags can be employed. By way of example only, suitable fluorescent antibody tags include, but are not limited to, quantum dots, Alexa Fluors® (available from Life Technologies™, Grand Island, N.Y.), fluorescein, rhodamine, Oregon green, pyrene, and HiLyte™ Fluor dyes (available from AnaSpec, Inc., Fremont, Calif.).

In step 404, the sample mixture is introduced to the nanoDLD array. As described above, the sample mixture can be introduced at the top of the array, with the direction of flow being from the top to the bottom of the array. It is notable that individual antibodies are approximately 10 nanometers (nm) in diameter and, based on the size threshold (see above), would maintain a "zig-zag" mode through the array. However, upon binding to its target phosphoprotein in a sample, the (antibody+phosphoprotein) complex size exceeds the threshold and enters a "bumping" mode. See, for example, FIG. 3. As shown in FIG. 3, only the phosphorylated proteins (labeled with "P") form a complex with the fluorescently-labeled phospho-specific antibody. Due to the size threshold, the antibody-phosphoprotein complex will enter a "bumping" mode along the direction of flow, while the smaller non-phosphorylated proteins maintain a "zig-zag" mode through the array.

In step 406, the "bumping" fraction is collected separately from the "zig-zag" fraction. In this example, it is the "bumping" fraction that will contain the (fluorescently-labeled) antibody-phosphoprotein complex, whereas the "zig-zag" fraction contains non-phosphorylated proteins, as well as individual (unbound) antibodies, contaminants, etc. Depending on the particular application at hand, the desired fraction (in this case the "bumping" fraction) can be collected, while the other (in this case the "zig-zag" fraction) can be either (separately) collected or discarded. For instance, sample mixtures may be run through the nanoDLD array multiple times, optionally using one or more different separation techniques to further purify the sample. Thus, in this example, it may be desirable to collect the "zig-zag" fraction for further purification.

In step 408, the collected "bumping" fraction is analyzed and processed. For instance, the fluorescent signal from the bumping antibody-phosphoprotein complex can be detected and quantified to determine the number of phosphoproteins in the sample. By way of example only, the fluorescent signal can be detected using a diode-induced fluorescence detector. Purified and concentrated phosphoprotein can also be collected from the bumped fraction.

Figure 5:
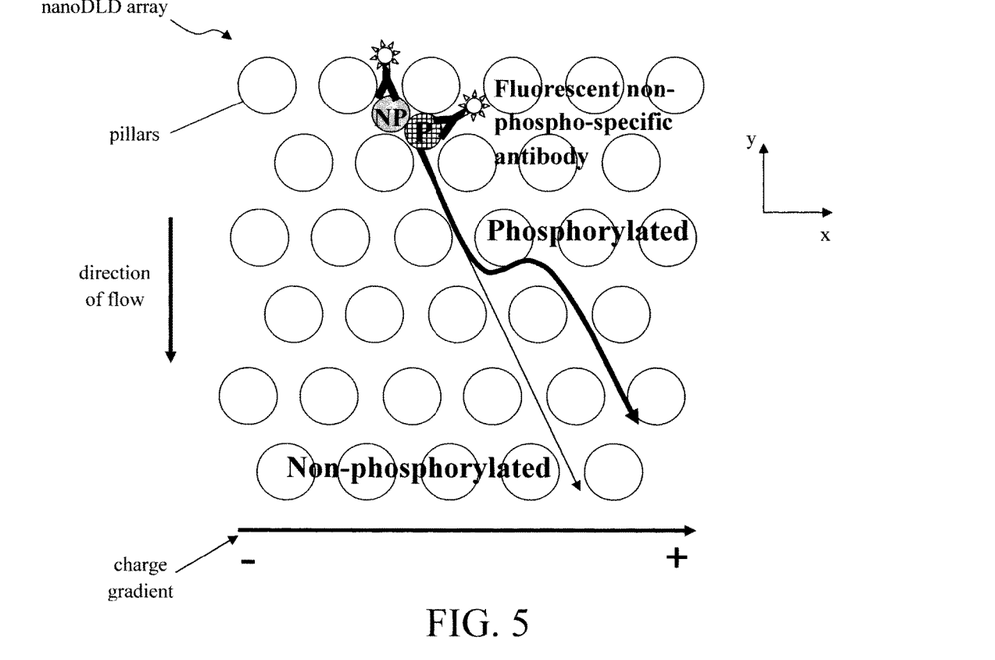
FIG. 5 is a diagram illustrating the present nanoDLD array being used for detection, quantification, and purification of phosphoproteins with a non-phospho-specific antibody and charge separation according to an embodiment of the present invention.

So far, it has been assumed that a phosphor-specific antibody is available. However, the case may arise where such a phosphor-specific antibody is not available. This situation is addressed by way of reference to FIG. 5 and methodology 600 of FIG. 6 which will be described together. FIG. 5, for instance, illustrates detection and quantification of phosphoproteins with a fluorescent-tagged, non-phospho-specific antibody and charge separation.

Antibodies bind by recognizing specific structures. To use an illustrative example, there are some antibodies that just recognize the phosphotyrosine structure, for instance, and therefore bind to all phosphotyrosines on any protein that has one. However, there are other antibodies that recognize both the phosphotyrosine and its surrounding structure within the context of a protein, so it only recognizes a specific phosphorylated tyrosine residue on a specific protein. The latter would be more useful for the present analysis since a generic phosphotyrosine antibody would recognize all proteins with phosphotyrosine in addition to the single protein of interest in the analysis.

Figure 6:
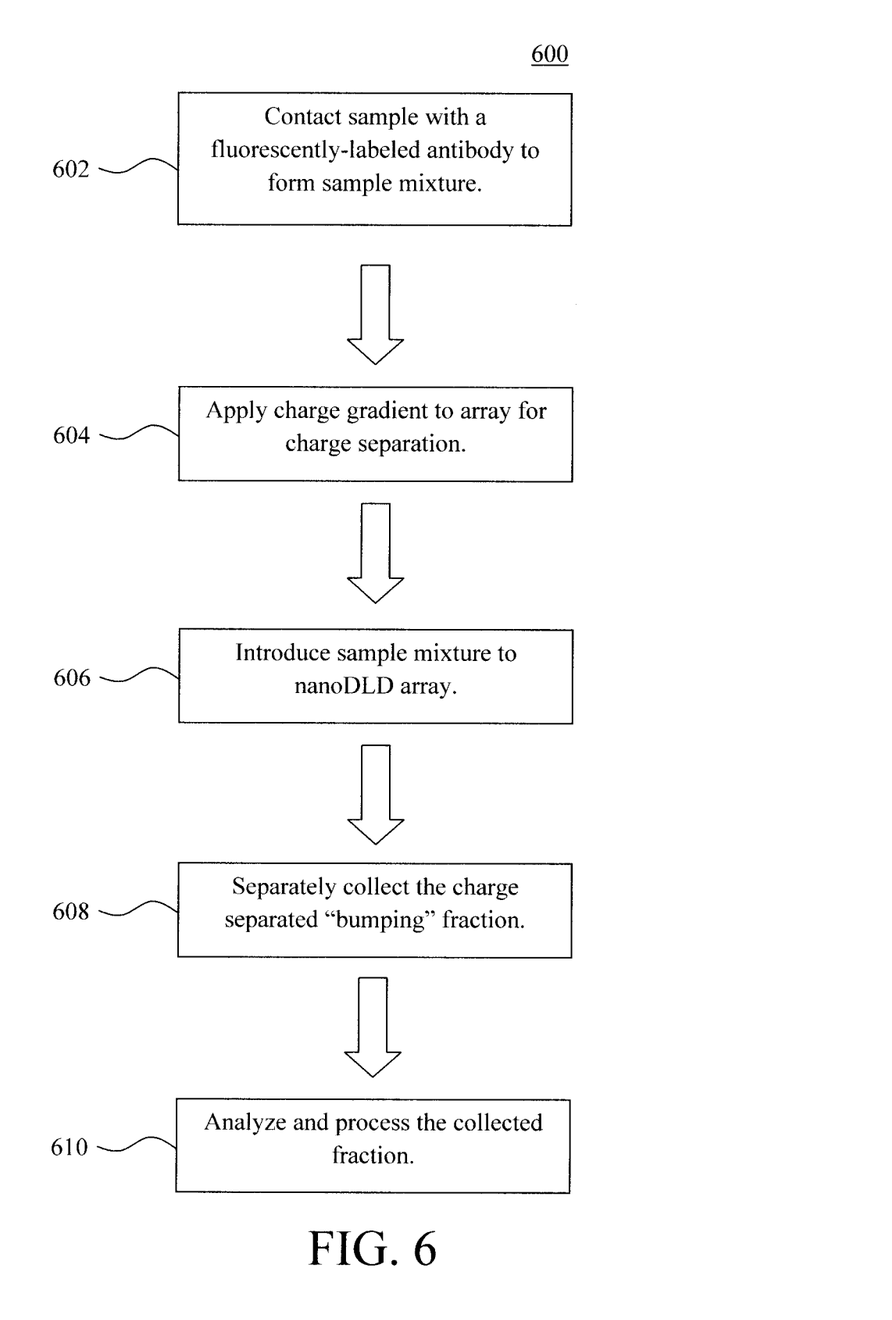
FIG. 6 is a diagram illustrating an exemplary methodology for detection, quantification, and purification of phosphoproteins with a non-phospho-specific antibody and charge separation according to an embodiment of the present invention.

The process begins in the same general manner as described above, however since a phospho-specific antibody is not available then an antibody against another epitope on the target protein (i.e., another antibody against the target protein) can be used. Namely, in step 602 of methodology 600, a sample is contacted with a fluorescently-labeled antibody. In this case, the antibody is not phospho-specific, but rather is specific for another epitope on the protein. Thus, the antibody used in this example is specific for a particular protein, regardless of whether the protein is phosphorylated or non-phosphorylated.

As provided above, step 602 can be carried out simply by mixing the (fluid) sample with a solution containing the fluorescently-labeled antibody to form a sample mixture. In the same manner as above, the complex formed when the antibody binds to the protein target exceeds the threshold size, causing the antibody-phosphoprotein complex to enter a "bumping" mode along the direction of flow through the array.

However, since the antibody being used is not phospho-specific then both phosphorylated and non-phosphorylated proteins will enter the "bumping" mode. Thus, to further increase the specificity of the separation, in step 604 a charge gradient is applied to the array. See FIG. 5. As described above, the charge gradient is applied perpendicular to the direction of flow and, as the sample mixture flows through the array, negatively charged particles (in this case the phosphorylated proteins) will migrate toward the positively charged side of the gradient (in this case the right side of the array—see FIG. 5) and the positively charged or uncharged particles (in this case the non-phosphorylated proteins) will migrate toward the negatively charged side of the gradient (in this case the left side of the array—see FIG. 5).

In step 606, the sample mixture is introduced to the nanoDLD array. As described above, the sample mixture can be introduced at the top of the array, with the direction of flow being from the top to the bottom of the array. The antibody-phosphoprotein complex will enter a "bumping" mode. See FIG. 5. As shown in FIG. 5, the antibody-phosphoprotein complexes include both phosphorylated proteins (labeled with "P") and non-phosphorylated proteins (labeled with "NP"), both in "bumping" mode. However, due to the charge gradient across the array, the negatively charged complexes (i.e., the phosphoproteins) are shifted even further to the right side of the array, thus effectively separating the phosphorylated from the non-phosphorylated proteins.

In step 608, the charge separated "bumping" fraction is collected. Namely, there will be two separate "bumping" streams and the particles in the furthest (phosphorylated stream) will be collected. As described above, the other output from the array can be (separately) collected for further purification or discarded.

In step 610, the collected charge separated "bumping" fraction is analyzed and processed. For instance, the fluorescent signal from the bumping antibody-phosphoprotein complex can be detected and quantified to determine the number of phosphoproteins in the sample. Purified and concentrated phosphoprotein can also be collected from the bumped fraction.

Figure 7:
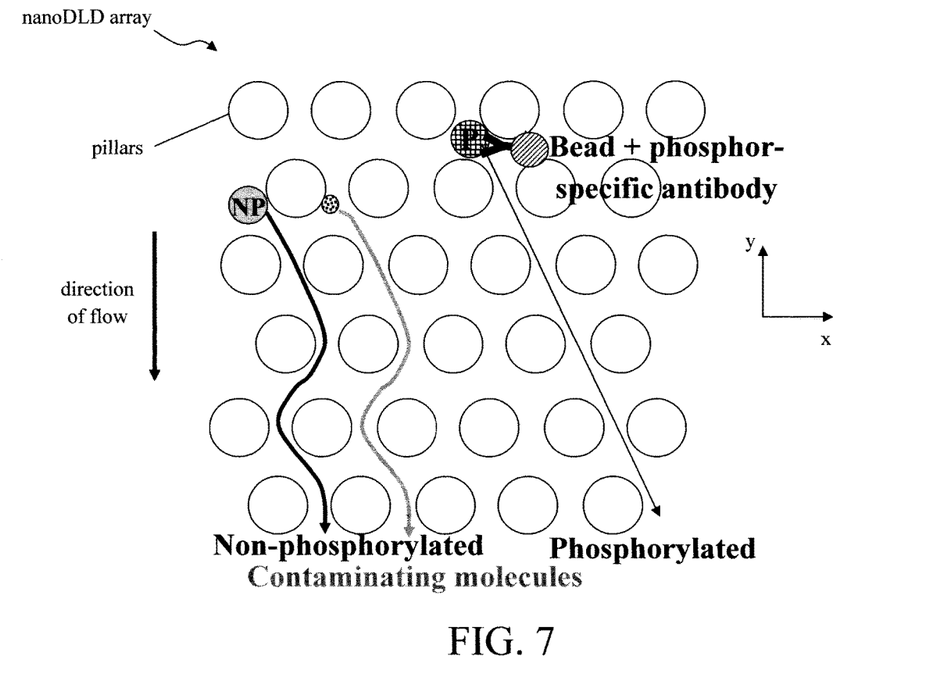
FIG. 7 is a diagram illustrating the present nanoDLD array being used for detection, quantification, and purification of phosphoproteins with a phospho-specific antibody and nano or micro bead according to an embodiment of the present invention.

Up to this point it has been assumed that there is a significant enough size difference between the antibody-phosphoprotein complex and the non-phosphorylated protein and/or other contaminating molecules such that these particles can be separated by size. In some instances, however, the size difference of one or more of these molecules from the antibody-phosphoprotein complex may not be significant enough to resolve them in the array. As a solution, techniques are provided herein to amplify the size of the antibody-phosphoprotein complex. According to an exemplary embodiment, the size of the antibody-phosphoprotein complex is amplified with antibody-coated nano or micro beads. See FIG. 7 and methodology 800 of FIG. 8, which will be described together. FIG. 7, for instance, illustrates purification with a phospho-specific antibody and nano or micro bead (e.g., polystyrene beads). By amplifying the size of the antibody-phosphoprotein complex, complete bumping and purification with the nanoDLD array can be achieved.

Figure 8:
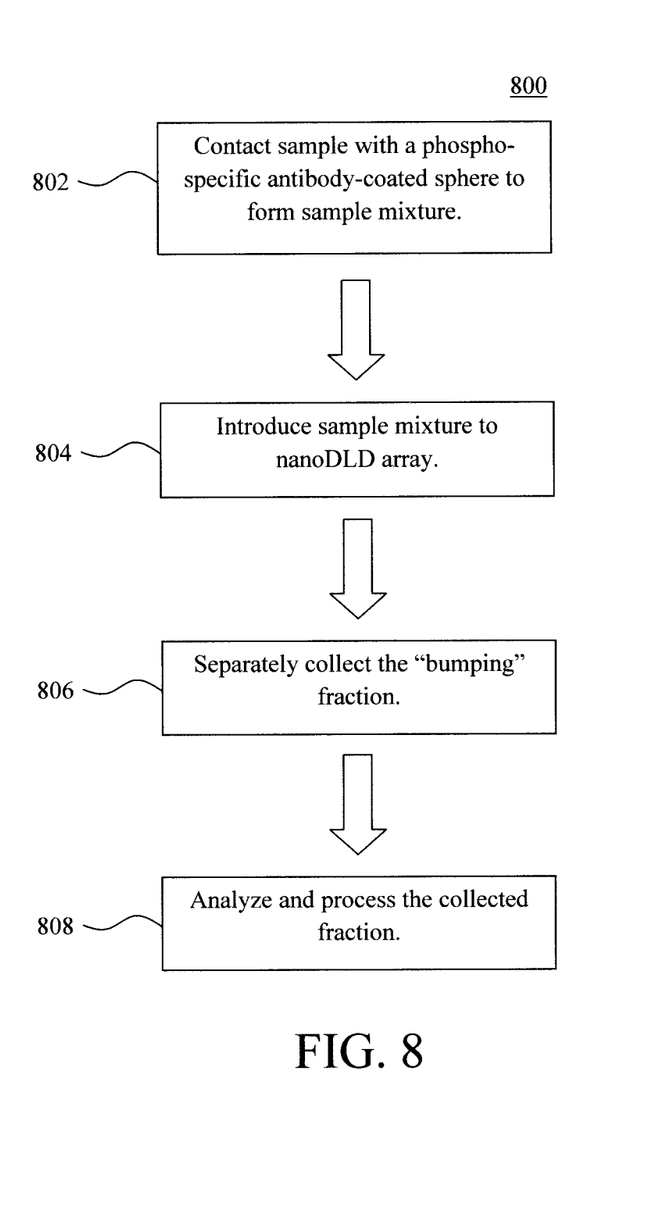
FIG. 8 is a diagram illustrating an exemplary methodology for detection, quantification, and purification with a phospho-specific antibody and nano or micro bead according to an embodiment of the present invention.

In step 802 of methodology 800, a sample is contacted with phospho-specific antibody-coated micro- or nano-spheres. According to an exemplary embodiment, the micro- or nano-beads are polystyrene beads having diameters in the micrometer or nanometer range, respectively. While the distinction between micro- and nano- is somewhat arbitrary, for illustrative purposes only, a micro-bead might have a diameter ranging from about 1 micrometer (μm) to 1,000 μm, and ranges therebetween, and a nano-bead might have a diameter ranging from about 1 nm to about 100 nm, and ranges therebetween. As shown in FIG. 7, the micro- or nano-beads bind to the phosphoprotein via the phospho-specific antibody on the surface of the beads.

According to an exemplary embodiment, the antibody coating on the micro- or nano-beads is achieved through covalent linkages or through the use of protein A/G-coated polystyrene beads which bind to antibodies in a high-affinity interaction. Protein A or G are common affinity binding proteins since they readily bind the Fc regions of a variety of different antibodies.

As provided above, step 802 can be carried out simply by mixing the (fluid) sample with a solution containing the phospho-specific antibody-coated beads to form a sample mixture. The phospho-specific antibody-coated beads will form a complex with the phosphoproteins in the sample. The presence of the beads will amplify the size of the complex relative to the non-phosphorylated proteins and other contaminants in the sample. The goal is have the phospho-specific antibody-coated bead+phosphoprotein complex exceed the threshold size and thereby enter a "bumping" mode along the direction of flow through the array, while the non-phosphorylated proteins and other contaminants in the sample remain in a "zig-zag" mode.

In step 804, the sample mixture is introduced to the nanoDLD array. As described above, the sample mixture can be introduced at the top of the array, with the direction of flow being from the top to the bottom of the array. The antibody-coated bead+phosphoprotein complex will enter a "bumping" mode. See FIG. 7. As shown in FIG. 7, the antibody-coated beads will form complexes only with the phosphorylated proteins (labeled with "P"). Further, the beads amplify the size difference between the complexes and the non-phosphorylated proteins (labeled with "NP") and other molecules such as contaminants.

In step 806, the "bumping" fraction is collected separately from the "zig-zag" fraction. In this example, it is the "bumping" fraction that will contain the antibody-coated bead+phosphoprotein complex, whereas the "zig-zag" fraction contains non-phosphorylated proteins, as well as individual (unbound) antibodies, contaminants, etc. As described above, the other output from the array can be (separately) collected for further purification or discarded.

In step 808, the collected "bumping" fraction is analyzed and processed. For instance, purified and concentrated phosphoprotein can be collected from the bumped fraction.

In the example described in accordance with FIG. 7 and FIG. 8 a phosphor-specific antibody was used. However, the same size amplification techniques can be employed in the case where a phosphor-specific antibody is not available and an antibody against another epitope on the target protein is used. As described above, this will select both phosphorylated and non-phosphorylated proteins for "bumping" mode. However, a charge gradient across the array can be used to further distinguish negatively charged (phosphorylated) proteins from positively charged or non-charged (non-phosphorylated) proteins.

Figure 9:
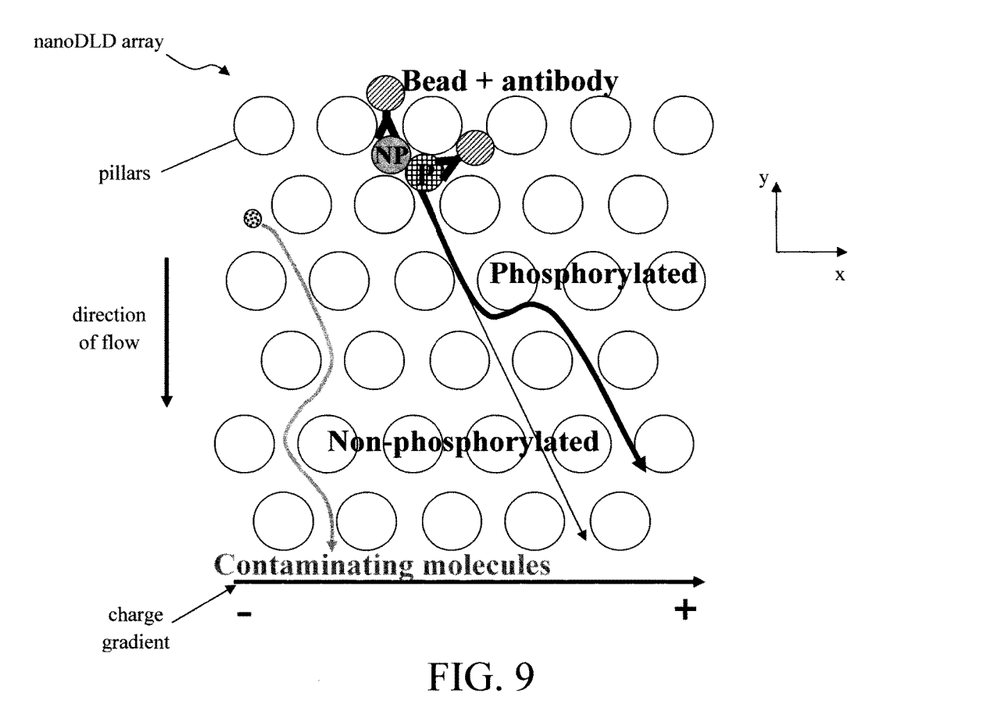
FIG. 9 is a diagram illustrating the present nanoDLD array being used for detection, quantification, and purification of phosphoproteins with a non-phospho-specific antibody and nano or micro bead along with charge separation according to an embodiment of the present invention.
Figure 10:
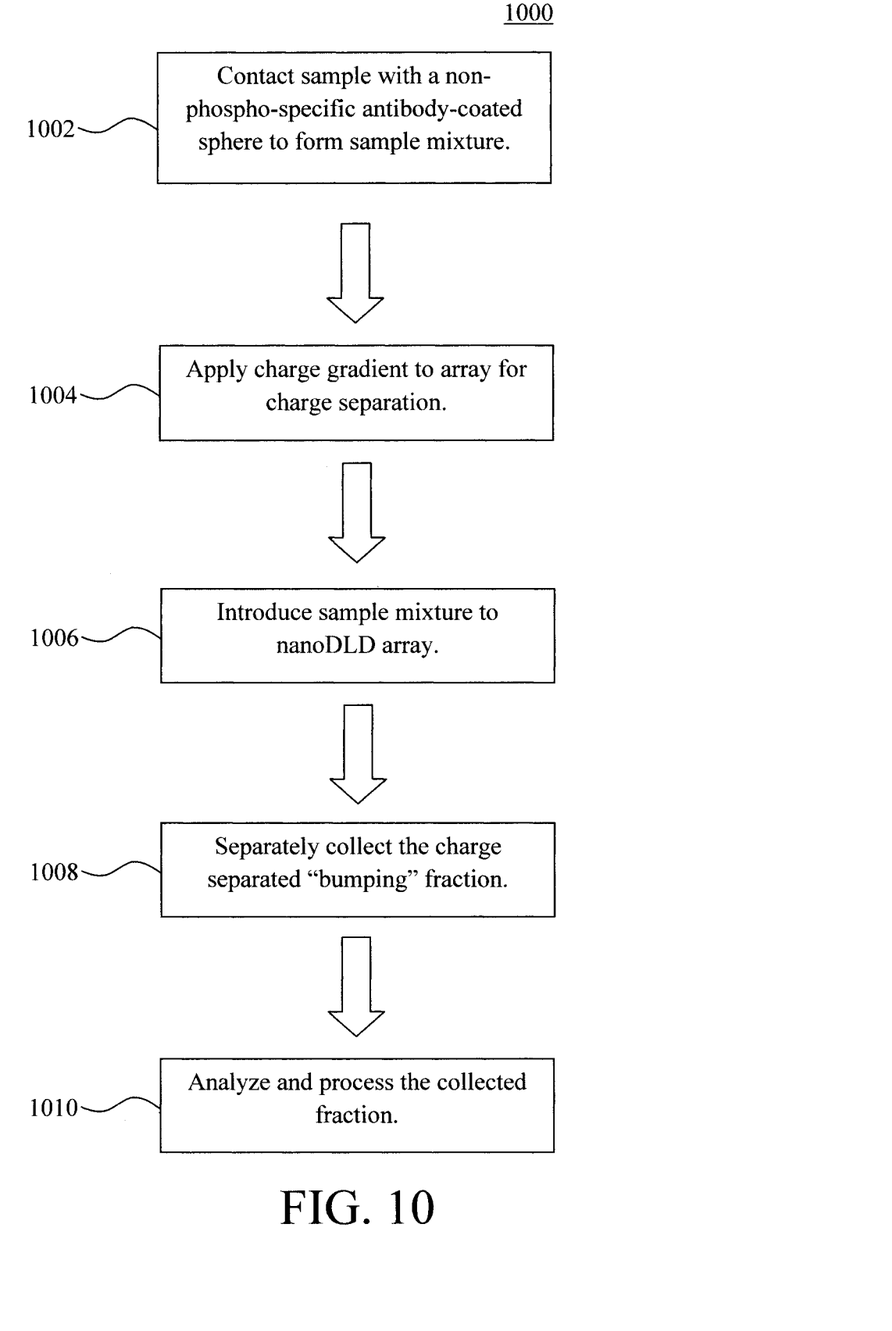
FIG. 10 is a diagram illustrating an exemplary methodology for detection, quantification, and purification of phosphoproteins with a non-phospho-specific antibody and nano or micro bead along with charge separation according to an embodiment of the present invention.

This situation is addressed by way of reference to FIG. 9 and methodology 1000 of FIG. 10 which will be described together. FIG. 9, for instance, illustrates detection and quantification of phosphoproteins with a non-phospho-specific antibody and nano or micro bead along with charge separation.

In step 1002 of methodology 1000, a sample is contacted with non-phospho-specific antibody-coated micro- or nano-beads (e.g., polystyrene beads). As provided above, step 1002 can be carried out simply by mixing the (fluid) sample with a solution containing the non-phospho-specific antibody-coated beads to form a sample mixture. The complex formed when the non-phospho-specific antibody-coated beads bind to the protein target exceeds the threshold size, causing the non-phospho-specific antibody-coated bead+phosphoprotein complex to enter a "bumping" mode along the direction of flow through the array.

However, since the antibody being used is not phospho-specific then both phosphorylated and non-phosphorylated proteins will enter the "bumping" mode. Thus, to further increase the specificity of the separation, in step 1004 a charge gradient is applied to the array. See FIG. 9. As described above, the charge gradient is applied perpendicular to the direction of flow and, as the sample mixture flows through the array, negatively charged particles (in this case the phosphorylated proteins) will migrate toward the positively charged side of the gradient (in this case the right side of the array—see FIG. 9) and the positively charged or uncharged particles (in this case the non-phosphorylated proteins) will migrate toward the negatively charged side of the gradient (in this case the left side of the array—see FIG. 9).

In step 1006, the sample mixture is introduced to the nanoDLD array. As described above, the sample mixture can be introduced at the top of the array, with the direction of flow being from the top to the bottom of the array. The non-phospho-specific antibody-coated bead+phosphoprotein complexes will enter a "bumping" mode, while the smaller molecules (such as contaminants) remain in a "zig-zag" mode. See FIG. 9. As shown in FIG. 9, the antibody-phosphoprotein complexes include both phosphorylated proteins (labeled with "P") and non-phosphorylated proteins (labeled with "NP"), both in "bumping" mode. However, due to the charge gradient across the array, the negatively charged complexes (i.e., the phosphoproteins) are shifted even further to the right side of the array, thus effectively separating the phosphorylated from the non-phosphorylated proteins.

In step 1008, the charge separated "bumping" fraction is collected. Namely, there are two separate "bumping" streams and the particles in the furthest (phosphorylated stream) will be collected. As described above, the other output from the array can be (separately) collected for further purification or discarded.

In step 1010, the collected charge separated "bumping" fraction is analyzed and processed. For instance, the purified and concentrated phosphoprotein can be collected from the bumped fraction.

As highlighted above, any of the above-described techniques can be used for the purification, detection, and quantification of phosphoproteins from bodily fluids, large-scale cell lysate, and in vitro samples. Additionally, this can also be accomplished using a single cell lysed within the array. See, for example, methodology 1100 of FIG. 11. For instance, in step 1102 of methodology 1100, any of the above-described fluorescent tagged antibody, antibody-bead set-ups can be pre-loaded onto the array. By way of example only, a loading reservoir can be present upstream from the pillar array (i.e., along the direction of flow) in which the antibody or antibody bead set-up is preloaded (i.e., placed prior to use). See, for example, FIG. 12—described below. Interaction of the proteins with the pre-loaded antibody can occur by introducing the sample to nanoDLD array via the loading reservoir. A pre-loaded reservoir can be used in accordance with any of the above-described processes as a substitute for having to separately mix the sample and a solution of the antibody before introducing the mixture to the nanoDLD array.

Figure 11:
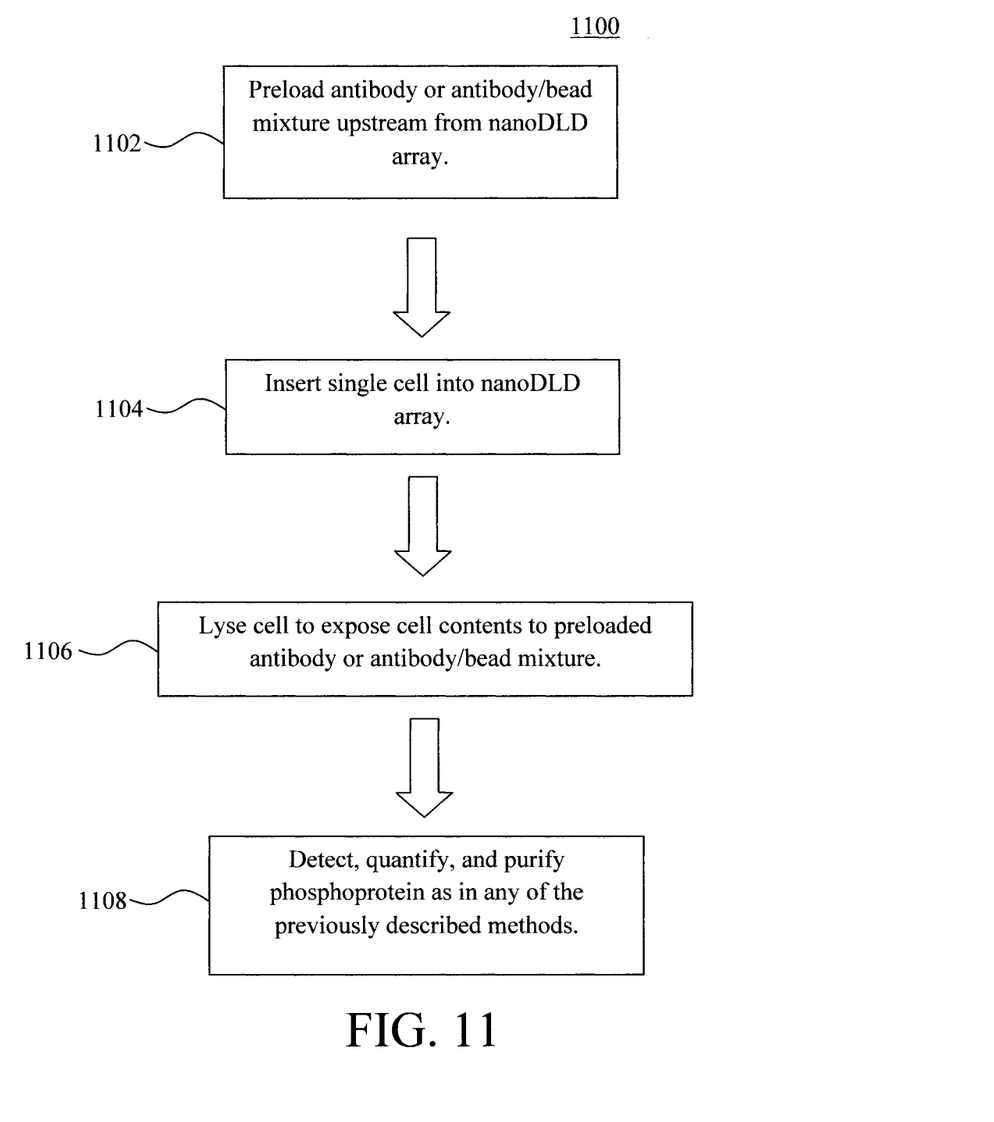
FIG. 11 is a diagram illustrating an exemplary methodology for detection, quantification, and purification of phosphoproteins using preloaded antibody or antibody/bead mixture and cell lyses within the array according to an embodiment of the present invention.

In this particular example, a single cell is inserted into the array (e.g., into the pre-loaded reservoir) (see step 1104) and then the cell is lysed using either physical lysis from pressure or chemical lysis from low-concentration detergent or surfactant such as NP-40 (nonyl phenoxypolyethoxylethanol) or Triton X-100 (4-(1,1,3,3-Tetramethylbutyl)phenyl-polyethylene glycol) (see step 1106). The contents of the lysed cell will encounter the antibody or antibody/bead mixture and purification, detection, and quantification will occur as described above (see step 1108). This process can be applied in instances of cell heterogeneity, such as in tumor cells.

Figure 12:
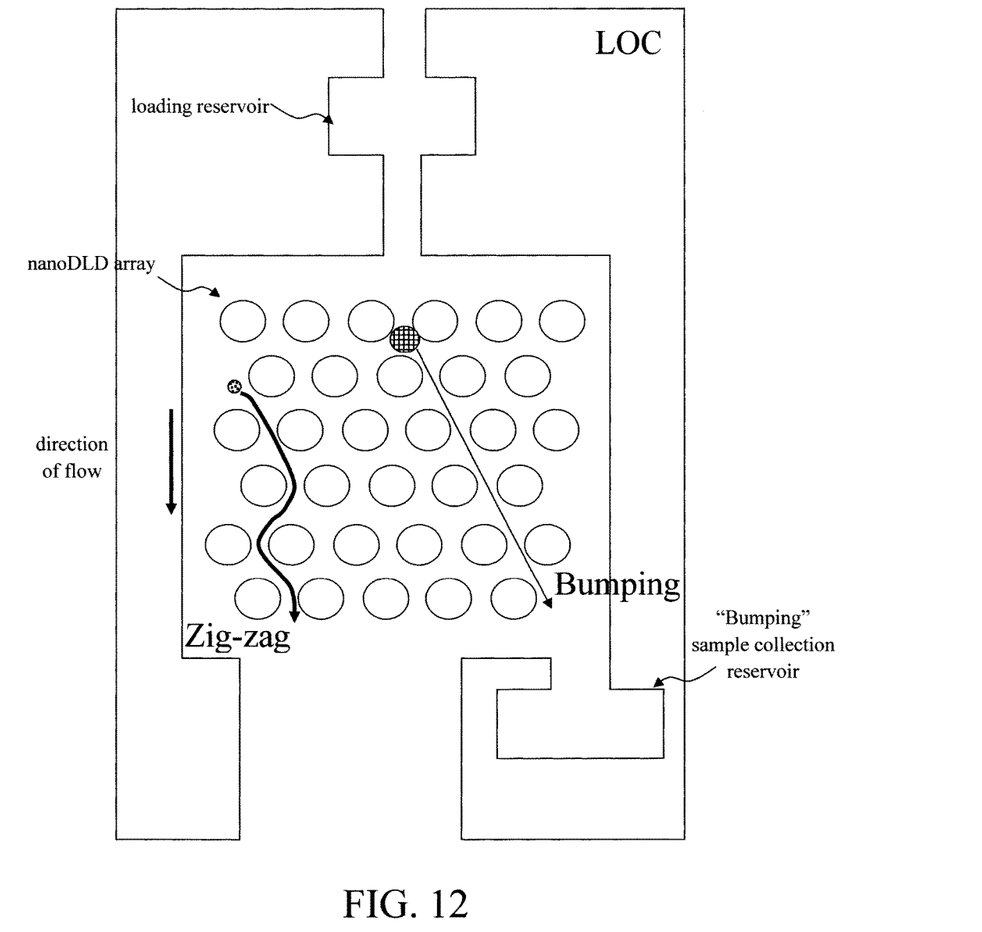
FIG. 12 is a diagram illustrating an exemplary lab-on-a-chip (LOC) according to an embodiment of the present invention.

FIG. 12 is a diagram illustrating an exemplary lab-on-a-chip or LOC design incorporating the above-described nanoDLD array. As shown in FIG. 12, a loading reservoir (for preloading the antibody or antibody/bead mixture) is located upstream (along the direction of flow) from the nanoDLD array. As described above, interaction of the proteins with the pre-loaded antibody can occur by introducing the sample to nanoDLD array via the loading reservoir. A sample collection reservoir is located downstream (along the direction of flow) from the nanoDLD array. The sample collection reservoir allows for samples to be binned and isolated from the zig-zag fraction. In this example, a collection reservoir is present to collect the "bumping" fraction, while the "zig-zag" fraction passes out of the bottom of the chip. However, a separate collection reservoir can also be included to collect the "zig-zag" fraction, if so desired.

Although illustrative embodiments of the present invention have been described herein, it is to be understood that the invention is not limited to those precise embodiments, and that various other changes and modifications may be made by one skilled in the art without departing from the scope of the invention.

What is claimed is:

1. A method for purifying a protein sample, the method comprising:
   introducing a mixture comprising the protein sample and an antibody conjugated to a microbead to a deterministic lateral displacement (DLD) array comprising a plurality of pillars separated by a gap, wherein the antibody conjugated to the microbead and proteins in the protein sample bind to form protein-antibody-microbead complexes having a size that is greater than a size threshold of 500 nm created by the gap which permits size-based separation of the protein-antibody-microbead complexes as the mixture flows through the DLD array, with the protein-antibody-microbead complexes passing through the DLD array in a bump mode and unbound proteins, which are smaller than the size threshold created by the gap, passing through the DLD array in a zig-zag mode;
   applying a negative to positive charge gradient to the DLD array for charge separation of the protein-antibody-microbead complexes, wherein the negative to positive charge gradient is applied to the DLD array perpendicular to a direction of flow of the mixture through the DLD array; and
   collecting a purified protein sample containing the protein-antibody-microbead complexes from the DLD array into a collection reservoir located downstream from the DLD array at a positive end of the negative to positive charge gradient,
   wherein the microbeads are selected such that the protein-antibody-microbead complexes are greater in size than the size threshold and smaller in size than the gap.

2. The method of claim 1, wherein the gap is from about 1 micrometer to about 5 micrometers.

3. The method of claim 1, wherein the proteins in the protein sample comprise both phosphorylated proteins and non-phosphorylated proteins.

4. The method of claim 3, wherein the antibody comprises a phospho-specific antibody.

5. The method of claim 3, wherein antibody comprises a non-phospho-specific antibody.

6. The method of claim 1, wherein the microbeads are polystyrene beads.

7. The method of claim 1, wherein the antibody is labeled with a fluorescent tag.

8. The method of claim 1, further comprising:
   analyzing the purified protein sample collected from the DLD array.

9. The method of claim 1, further comprising:
   mixing the protein sample with a solution containing the antibody conjugated to the microbead to form the mixture prior to introducing the mixture to the DLD array.

10. The method of claim 1, further comprising:
preloading the antibody conjugated to the microbead upstream from the DLD array.

\* \* \* \* \*